United States Patent
Rahman et al.

(10) Patent No.: US 7,166,063 B2
(45) Date of Patent: Jan. 23, 2007

(54) BRACE COMPLIANCE MONITOR

(75) Inventors: Tariq Rahman, Wilmington, DE (US);
J. Richard Bowen, Wilmington, DE (US)

(73) Assignee: The Nemours Foundation, Wilmington, DE (US)

( * ) Notice: Subject to any disclaimer, the term of this patent is extended or adjusted under 35 U.S.C. 154(b) by 0 days.

(21) Appl. No.: 11/025,783

(22) Filed: Dec. 30, 2004

(65) Prior Publication Data

US 2005/0165336 A1    Jul. 28, 2005

Related U.S. Application Data

(63) Continuation of application No. 10/260,526, filed on Oct. 1, 2002, now Pat. No. 6,890,285.

(60) Provisional application No. 60/325,565, filed on Oct. 1, 2001, provisional application No. 60/384,112, filed on May 31, 2002.

(51) Int. Cl.
*A63B 21/00*    (2006.01)
*A63B 22/00*    (2006.01)

(52) U.S. Cl. .................. 482/8; 482/1; 482/9; 600/587; 602/1; 602/2

(58) Field of Classification Search ................ 482/1–9, 482/900–902; 600/587; 128/869, 882; 602/1, 602/2, 5, 13–29
See application file for complete search history.

(56) References Cited

U.S. PATENT DOCUMENTS 6,436,058 B1 * 8/2002 Krahner et al. ............. 600/587
6,540,707 B1 * 4/2003 Stark et al. .................. 602/13

* cited by examiner

*Primary Examiner*—Glenn E. Richman
(74) *Attorney, Agent, or Firm*—McGuireWoods LLP

(57) ABSTRACT

A brace compliance monitor is disclosed that includes a compliance sensor, a signal processor, and a display. Compliance data is displayed on the display to provide the patient or subject with immediate compliance information on whether they have been wearing the brace for the specified period and in the specified manner. The brace compliance monitor may also include a secondary sensor such as a tilt sensor, a pressure sensor, a force sensor, an acceleration sensor, or a velocity sensor. The secondary sensors may provide additional compliance data to the patient and health car provider.

7 Claims, 3 Drawing Sheets

BRACE COMPLIANCE MONITOR

RELATED APPLICATIONS

The present continuation application is related to and claims, under 35 U.S.C. § 120. the benefit of U.S. patent application Ser. No. 10/260,526, filed Oct. 1, 2002, now U.S. Pat. No. 6,890,285 which is expressly incorporated fully herein by reference and which is based on U.S. Provisional Application No. 60/325,565, filed on Oct. 1, 2001 and U.S. Provisional Application No. 60/384,112, filed on May 31, 2002, each herein incorporated by reference in their entireties.

FIELD OF THE INVENTION

The present invention is directed to a brace compliance monitor system. In particular, the present invention is directed to a brace compliance monitoring system that provides immediate feedback to the patient.

BACKGROUND OF THE INVENTION

Brace compliance is a significant issue in the care and treatment of many disorders. Failure of a patient to comply with health care providers instructions to wear a brace for a prescribed period of time inhibits the care and recovery of the patient. In addition to slow recovery or treatment, non-compliance by the patient leads to increased health-care costs. In some instances, non-compliance can lead to additional complications requiring additional care and treatment.

Previous compliance monitors have outfitted braces with a sensor for detecting when the patient is wearing the brace. These monitors may use a temperature sensor that detects ambient temperature when the brace is not being worn and an increased temperature when the brace is being worn. The data is recorded as a function of time to determine how long the patient has worn the brace and stored on a data storage device located on the brace. When the patient visits the health care provider, the health care provider can connect the data storage device to a computer, download the stored data, and then analyze the collected data to determine how long the patient wore the brace. From this data, the health care provider can determine whether the patient has complied with the prescribed time period for wearing the brace.

While this system can determine whether a patient complied with a prescribed time period, the analysis of the data is typically performed after the treatment period is over or at some time later during the treatment period when the patient visits the health care provider. Unless the patient is diligent about tracking the amount of time they have worn the brace, the patient only gets compliance information when they visit the health care provider, the data is downloaded and analyzed to asses compliance. It would be advantageous to have a compliance monitor that provides the patient with instant, immediate, or readily available feedback on whether they are in compliance with the prescribed treatment. In this way, non-compliance is recognized by the patient much earlier in the treatment, providing the patient with the opportunity to correct compliance deficiencies.

SUMMARY OF THE INVENTION

It is an object of the present invention to provide a brace compliance monitor that gives the patient immediate, instant or readily available feedback on compliance information. Accordingly, the present invention includes a brace compliance monitor having a compliance sensor, a display, and a signal processing unit in communication with the compliance sensor and compliance display, where the signal processing unit receives and stores data from the compliance sensor as a function of time, compares the data received from the compliance sensor with a compliance protocol to produce compliance data, and displays compliance data on the compliance display.

In certain embodiments the compliance sensor may be a temperature sensor, or a capacitive sensor. Further, the display may be either an LCD display or an LED display.

In further embodiments, the brace compliance monitor may include a secondary sensor in communication with the signal processing unit, wherein the signal processor receives and stores data from the secondary sensor as a function of time. The secondary sensor may be one or more selected from the group consisting of a tilt sensor, a pressure sensor, a force sensor, an acceleration sensor, and a velocity sensor. In a preferred embodiment, data from the secondary sensor is compared to the compliance protocol and displayed on the display. In other embodiments the display is attached to the brace.

In certain preferred embodiments, the compliance sensor and the signal processing unit are attached to a brace. In some embodiments, the brace is a scoliosis brace.

DETAILED DESCRIPTION OF THE INVENTION

The present invention is directed to a brace compliance monitor that provides the patient with immediate or instant feedback on compliance data. The invention is applicable to virtually any type of brace that is being worn by a person in which compliance is an issue. These braces include scoliosis braces, braces for the neck, knee, ankle, shoulder, elbow, wrist, arm, leg, and other similar braces. While the invention is applicable to many different types of braces, the invention will be described in conjunction with a scoliosis brace.

Scoliosis is an abnormal curvature of the spine. Approximately four percent of all children between the ages of 10 and 14 have detectable scoliosi with adolescent idiopathic scoliosis being most common. The predominant non-operative treatment for scoliosis is spinal bracing. A brace such as the Wilmington brace, the Milwaukee brace, and the Boston brace is typically worn 23 hours a day until skeletal maturity. Wearing the brace usually induces phychosocial concerns for the child who appears different from their peers. As a result, many children have difficulty complying with the prescribed time of brace wear. Recently, it has been learned that less than 23 hours per day brace wear can achieve good control of scoliosis, provided that the prescribed brace compliance was adhered to.

Figure 1:
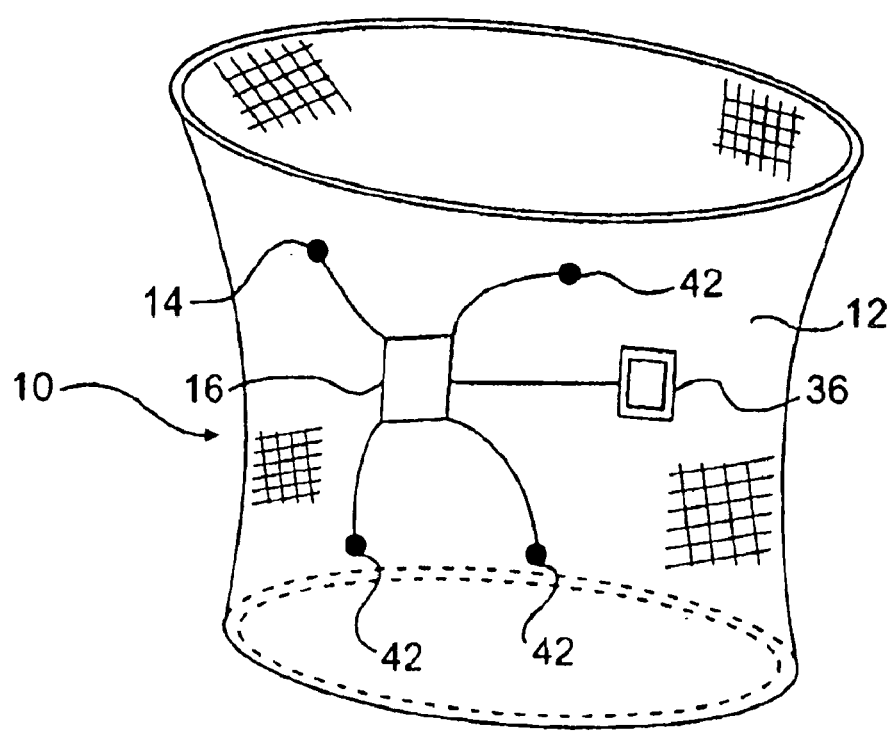
FIG. 1 illustrates a scoliosis brace with a compliance monitor in accordance with one embodiment of the present invention.

With reference now to FIG. 1, there is shown a brace compliance monitor 10 on a scoliosis brace 13 in accordance with one embodiment of the present invention. The brace compliance monitor 10 includes a compliance sensor 14. The compliance sensor 14 is a sensor that can distinguish when the brace is on or off of the patient. Suitable compliance sensors include, but are not limited to temperature sensors, light sensors, capacitive sensors and the like. With respect to a temperature sensor, the temperature sensor can distinguish when the brace is being worn by monitoring the temperature at a point near the brace-skin interface. If the brace is being worn, the temperature will be elevated relative to ambient temperature conditions. If the brace is not being worn, the temperature detected through the temperature sensor will be close to ambient temperature. Similarly, the capacitive sensor when close to a patient can determine when a person is wearing the brace. The compliance sensor 14 is connected to a signal processing unit 16 which collects and stores data from the compliance sensor 14. The size of the signal processing unit 16 may vary widely but is preferably as small as possible. The signal processing unit 16 should be of a size and configured such that is does not interfere with the operation or function of the brace.

Figure 2:
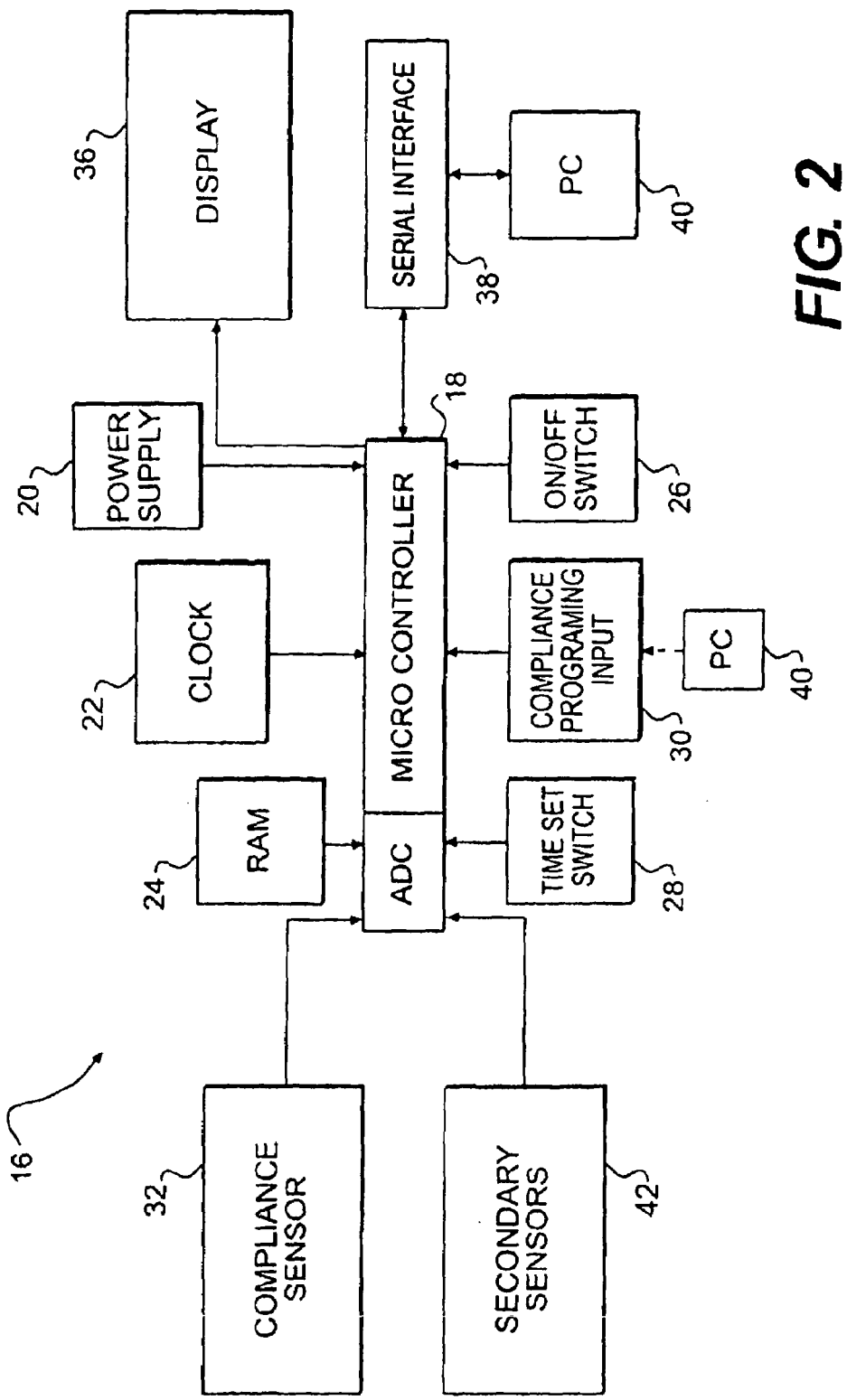
FIG. 2 illustrates a signal processing unit in accordance with one embodiment of the present invention.

With reference now to FIG. 2, the compliance signal processing unit 16 includes a circuit that has a microcontroller 18 connected to a power supply 20, a clock 22 and non-volatile random access memory (RAM) 24. The microcontroller 18 receives input from an on/off switch 26, clock set switch or switches 28, a compliance programming input 30, and the compliance sensor 32. Input from the compliance sensor 32 is received by the microcontroller 18 through an analog-to-digital converter (ADC) 34. The microcontroller 18 provides outputs to a compliance display 36, and may be connected through a computer interface 38, such as a serial connection or port for data transfer with a computer.

The microcontroller 18 receives and stores a compliance protocol for brace wear compliance through the compliance programming input 30. The compliance programming input 30 may be similar to a clock set switch where a sequence of buttons are depressed to program the compliance protocal in the compliance signal processing unit 16 or the compliance programming input may include a connection with a computer 40 for uploading the compliance protocol. Compliance protocols may vary widely. Some of the criteria used in the protocol may include the amount of time the brace is to be worn over a period of time such as a day, week, month, etc. as well as during activities or at rest.

The microcontroller 18 will receive data from the compliance sensor 32 as a function of time and compare the data with the compliance protocol to produce compliance data to determine if the collected data meets the requirements of the compliance protocol and thus, if the patient is in compliance with the protocol. The comparison is preferably made in a continuous fashion and is readily available so that the patient may know as soon as possible if they are in compliance with the protocol.

Figure 3:
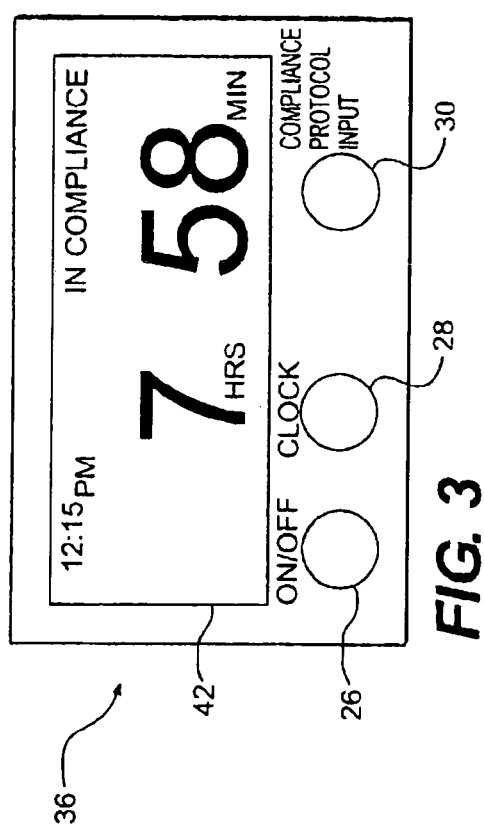
FIG. 3 illustrates a display panel for the compliance monitor in accordance with one embodiment of the present invention.
Figure 4:
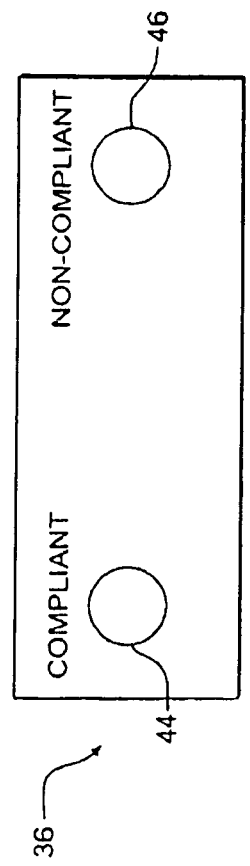
FIG. 4 illustrates a display panel for the compliance monitor in accordance with another embodiment of the present invention.

The microcontroller 18 provides compliance output information such as data from the compliance sensor and compliance data to a compliance display 36. With reference now to FIG. 3, the compliance display 36 may be an LCD screen 42 that displays information to the patient such as the amount of time the brace has been worn, how much longer the brace must be worn, and whether the compliance conditions are being met. The display 36 may also provide information such as the average daily wear time as well as current wear time for the brace. With reference to FIG. 4, the compliance display 36 may include an LED or series of LEDs that indicate to the patient weather the compliance conditions of the protocol are being met. For example, a green LED 44 would illuminate if the compliance conditions are being met and a red LED 46 would illuminate for non-compliance conditions.

The compliance display 36 is preferably located in a position that can be easily monitored. In preferred embodiments, the compliance display 36 is located at a visible location on the brace. In alternative embodiments, the compliance display could be located remotely from the brace by wire or wireless connections with the compliance signal processing unit.

In some instances it will be useful to monitor other properties associated with the wearing of a brace. For example, to be able to distinguish what the patient was doing while wearing the brace would help with treatment and provide health care providers additional important information regarding the treatment of the patient. . Accordingly, with reference to FIG. 1, in certain embodiments of the invention, it would be advantageous to provide at least one secondary sensor 42 that monitors properties other than whether the brace is being worn or not. The secondary sensors 42 may include, but are not limited to, a tilt sensor, an acceleration, a velocity sensor, a pressure or force sensor. The secondary sensor 42 would be located on an appropriate position on the brace for the type of sensor being used. The secondary sensor 42 may be secured to the brace and attached to the signal processing unit 16 through the ADC 34 for secondary data collection and storage. By collecting information from the secondary sensor in conjunction with the compliance sensor, the additional compliance dimension may be monitored by the health care provider and the patient.

When a tilt sensor is being used as a secondary sensor, information about the posture of the patient while wearing the brace could be determined. For example, the data collected would tell with the patient is sitting, lying down, standing, or walking. The posture of the patient may affect their biomechanics and consequently the effectiveness of the brace and treatment protocol.

An acceleration or velocity sensor could be used to monitor the level of activity of the patient. Determination of whether the patient was walking, running, etc. would be useful in evaluating the treatment protocol for the patient.

A pressure or force sensor may be used to obtain data about the forces imparted by the brace. This information could be used to make the brace more comfortable for the patient, thus increasing the likelihood of compliance. Further, the force or pressure data could be used to design a better more effective brace by reducing or eliminating areas of the brace where the forces are minimal or absent.

A combination of one or more of the same or different type of secondary sensors may be utilized in certain embodiments of the present invention.

It will therefore be readily understood by those persons skilled in the art that the present invention is susceptible to broad utility and application. Many embodiments and adaptations of the present invention other than those herein described, as well as many variations, modifications and equivalent arrangement, will be apparent from or reasonably suggested by the present invention and the foregoing description thereof, without departing from the substance or scope of the present invention.

Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims and the equivalents thereof.

What is claimed is:

1. A method of providing compliance feedback in a brace comprising the steps of:
   sensing whether the brace is in position on a user;
   outputting a compliance signal in response to said sensing step;
   sensing an attitude of the brace to generate attitude data;
   storing the compliance signal as compliance data;
   determining compliance based upon the compliance data and a predetermined compliance protocol; and
   outputting at least one of the compliance result and the attitude data.

2. The method according to claim 1 wherein said step of outputting occurs in response to user interaction.

3. The method according to claim 1 wherein said step of sensing the position of the brace comprises sensing at least one of temperature, light, and capacitance.

4. The method according to claim 1 wherein said step of sensing an attitude comprises sensing at least one of tilt, acceleration, velocity, pressure or force.

5. The method according to claim 4 wherein the attitude is at least one of sitting, lying down, standing, or walking.

6. The method according to claim 1 further comprising the steps of:
   storing the compliance data in a signal processor; and
   inputting the compliance protocol to the signal processor.

7. The method of claim 1 wherein the brace comprises a scoliosis brace.

* * * * *